United States Patent [19]

Leblanc et al.

[11] 3,936,585
[45] Feb. 3, 1976

[54] FIRE RETARDING TEXTILE MATERIALS
[75] Inventors: Robert Bruce Leblanc; Destin A. Leblanc, both of Wickford, R.I.
[73] Assignee: Robert Bruce Leblanc, East Greenwich, R.I.
[22] Filed: Dec. 5, 1973
[21] Appl. No.: 422,058

[52] U.S. Cl. ............... 428/921; 8/116 P; 8/196; 106/15 FP; 252/8.1; 260/606.5 P; 427/342; 427/390
[51] Int. Cl.² ........................................ D06M 13/44
[58] Field of Search .......... 260/606.5 P; 106/15 FP; 252/8.1; 117/136, 137, 62.2; 8/116 P, 115.7, 196; 427/390, 342; 428/921

[56] References Cited
UNITED STATES PATENTS

| | | | |
|---|---|---|---|
| 2,772,188 | 11/1956 | Reeves et al. | 117/136 |
| 2,809,941 | 10/1957 | Reeves et al. | 117/136 X |
| 2,812,311 | 11/1957 | Reeves et al. | 117/136 X |
| 2,983,623 | 5/1961 | Coates | 117/137 X |
| 3,276,897 | 10/1966 | Reeves et al. | 117/136 X |
| 3,698,854 | 10/1972 | Donaldson et al. | 117/137 X |
| 3,784,356 | 1/1974 | Wagner | 117/136 X |

*Primary Examiner*—Michael R. Lusignan
*Attorney, Agent, or Firm*—Burgess, Dinklage & Sprung

[57] ABSTRACT

A water soluble product suitable for rendering textile materials fire retardant is produced by condensing a poly (α-hydroxyalkyl)phosphorus compound of the formula $$(RCHOH)_n (RCHR')_{4-n} P-Y$$

or $$(RCHOH)_m (RCHR')_{3-m} P$$

and a nitrogen compound of the formula $RNH_2$, $HO-R''NH_2$ or

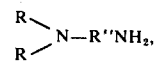

wherein
R is hydrogen or alkyl of 1 to 3 carbon atoms,
R' is OR or

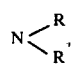

R'' is alkylene of 1 to 3 carbon atoms,
Y is at least one anion selected from the group consisting of chloride, sulfate, phosphate, acetate and formate,
n is an integer from 2 to 4, and
m is an integer from 2 to 3,
the phosphorus compound being present in about 0.5 to 6 times the molar amount of the nitrogen compound.

Advantageously the phosphorus compound is a tetrakis(hydroxy-methyl)phosphonium salt or a tris(hydroxymethyl) phosphine and is present in about 1 to 3 times the nitrogen compound which is preferably ammonia. The condensation product, dissolved in water, is padded onto a fabric, preferably a polyester-cotton blend, which is thereafter dried and cured thermally and/or chemically. The fabrics are fire retardant even after multiple launderings.

12 Claims, No Drawings

FIRE RETARDING TEXTILE MATERIALS

BACKGROUND OF THE INVENTION

The present invention relates to novel water soluble condensation products of methylol phosphorus compounds with nitrogen compounds, to the processes of using these water soluble materials to produce flame-retardant textile materials and to the flame-retardant textile materials so produced.

The practice of treating textile materials for flame retardance has assumed increasing importance with the adoption of federal, state and municipal legislation designed to protect the public from unreasonable hazards of flammable textile products.

The compound tetrakis(hydroxymethyl) phosphonium chloride is known to be a basis for flame-retardant finishes for cellulosic fabrics. Reeves and Guthrie in U.S. Pat. No. 2,809,941 used a solution of tetrakis(hydroxymethyl)phosphonium chloride, melamine-formaldehyde resin and urea to treat cotton fabrics by a pad-dry-cure method. This treatment and slight modifications of it have been used commercially to give cotton fabrics flame-retardance durable to multiple launderings. The treatment, however, causes high fabric strength losses and makes the fabrics too stiff to use except for certain areas such as industrial cotton work clothing and tent liners.

Reeves and Guthrie in their later-filed U.S. Pat. No. 2,772,188 disclosed an improved process for forming an insoluble polymer of tetrakis(hydroxymethyl)phosphonium chloride in cellulosic fabrics by what is known as a chemical cure. In water there was made a prepolymer of tetrakis(hydroxymethyl)phosphonium chloride and either methylolmelamine or urea or phloroglucinol. This solution was padded onto cotton fabric. The fabric was dried and then treated with ammonia (chemical cure) to produce an insoluble polymer in and on the fabric. The fabric was fire retardant.

Coates in U.S. Pat. No. 2,983,623 improved on this process by using a chemical cure which consisted of treating impregnated fabric first with gaseous ammonia and then with aqueous $NH_3$. Pre-condensates were made by refluxing tetrakis(hydroxymethyl) phosphonium chloride in water containing either urea, melamine, a urea and thiourea mixture, dicyandiamide or guanidine. Water solutions of the pre-condensate were padded onto cotton fabric. The fabric was dried and subsequently put first into a gaseous ammonia chamber and then into an aqueous solution of ammonia to form an insoluble polymer in and on the fabric. This fabric was flame-retardant. The particular process using a tetrakis(hydroxymethyl)phosphonium chloride-urea pre-condensate has become commercial and is known as the "Proban" process. It is adequate for cellulosic textiles, but is not satisfactory for polyester-cotton blend fabrics.

Coates and Chalkey in U.S. Pat. No. 3,236,676 further simplified the process by using tetrakis(hydroxymethyl)phosphonium salts (abbreviated THP salts) neutralized with a base such as NaOH to a pH between 3 and 9.5 instead of the tetrakis(hydroxymethyl)phosphonium chloride-urea precondensate. Fabric was padded with the neutralized THP salt, dried and given a heat cure sufficient to fix the THP salt on the fabric. Subsequently the fabric was treated with ammonia to form an insoluble polymer in and on the fabric.

Beninate et al. in U.S. Pat. No. 3,607,356 improved on this process by omitting the heat cure to fix the THP salt prior to the treatment with gaseous ammonia. They neutralized THP salt with a base such as NaOH to a pH of about 7.5 to 7.9. They called this neutralized product THPOH. In reality a solution of THP salt neutralized in this way consists mostly of tris(hydroxymethyl)-phosphine (Reeves et al., Textile Chemist and Colorist 2, 283–285 (1970)). Cotton fabric was padded with an aqueous solution of this "THPOH" and dried to a moisture content of about the normal cotton moisture regain, or a little higher. This fabric was then subjected to an atmosphere of dry, gaseous ammonia to form an insoluble polymer in and on the fabric. They claimed this process would give flame-retardance not only to cellulosic fabrics and wool but also to polyester-cotton blends. This process has been commercialized and is adequate for cotton fabrics, but does not give adequate flame-retardance to a polyester-cotton blend containing more than 20% polyester.

LeBlanc and Gray (Textile Chemist and Colorist 3, 263–265 (1971)) did a study on the application of THPOH finish to polyester-cotton blends. They found that it is possible to give a minimum level of fire-retardance to blends which have no more than 12.5-25% polyester. Even at these levels of polyester, the treated fabrics were excessively stiffened by the treatment.

Tesoro (Textile Chemist and Colorist 5, 235–238 (1973) and NTIS-COM-73-11265) concluded that a satisfactory flame-retardant system for polyester-cotton should contain phosphorus and bromine and that the presence of nitrogen is not important.

Ciba-Geigy Corporation has disclosed developmental product, Pyrovatex 3762, for making polyester-cotton blends flame retardant (John Leddy and Rene Eckert, "Durable Flame Retardant Finishing of Cotton and Polyester-Cotton Blends", Proceedings of the 1973 Symposium on Textile Flammability, LeBlanc Research Corporation, East Greenwich, R.I.) From German Specification DOS 2,136,407 it appears the product, a "phosphonium oligomer" is a water-soluble self-condensation product of tetrakis(hydroxymethyl)phosphonium chloride. It can be applied to polyester-cotton blends by a pad-dry-cure-afterwash process. The padding solution contains the self-condensation product Pyrovatex 3762, a dimethylolmelamine, urea, a softener and a wetting agent. The Pyrovatex 3762 has a highly objectionable phosphine-type odor during fabric processing and the processed fabrics are very stiff.

In British Pat. No. 761,985 ammonia is condensed with a THP salt but the product is a water-insoluble polymeric solid and is employed to treat cellulosic material as an emulsion in water.

In Chemical Abstracts Vol. 79 (1973) 20256x there is abstracted German DOS 2,242,681 which self-condenses tetrakis(hydroxymethyl)phosphonium chloride to remove water and leave a polymer which, with urea, forms a dispersible material for addition to viscose spinning dopes. In Chemical Abstracts Vol. 79 (1973) 20258z there is abstracted German DOS 2,242,682 wherein THPC is condensed with an amine such as dodecylamine in xylene to give a condensate. In Chemical Abstracts Vol. 79 (1973) 93383w there is abstracted German DOS 2,255,113 wherein THPC is simultaneously reacted with ammonia and urea. None of these treatments, however, is believed to be commericial.

Thus, while 50—50 or 65-35 polyester-cotton blend fabrics comprise about one-third of the total textile fabrics currently produced in the United States, at the present time there is no commercially available finish for flame-retarding such polyester-cotton blends. One of the problems is that the polyester polymer fiber has no reactive groups on it such as the hydroxyl groups on the cellulose polymer. When the polyester content of a fabric approaches 50%, the number of available hydroxyl groups on the fabric is decreased to such an extent that it becomes difficult to attach flame-retardant compounds onto the fabric. While Pyrovatex 3762 has more reactive methylol groups per molecule than do THP salts so that it can be polymerized with a resin such as dimethylolmelamine with a higher efficiency than THP salts, its disadvantages have been outlined hereinabove.

GENERAL DESCRIPTION OF THE INVENTION

It is accordingly an object of the present invention to provide compositions useful for flame retarding textile materials, especially polyester-cotton textile fabrics.

It is a further object to provide processes by which said compositions are used to flame retard textile materials.

It is a further object to provide flame retardant textile materials.

The materials or substrates to which this invention is applicable include textiles or webs formed of cotton, linen, regenerated cellulose, rayon, partially etherified and esterified cellulosic materials; textile blends of these fiber types with other fibers, such as polyester, nylon, acrylics, modacrylics, vinyon, wool, silk, etc.; other forms of cellulose such as wood and paper products; and proteinaceous textiles such as wool and silk. The textile materials may be in the form of fibers, yarns, fabrics (woven, non-woven, and knitted), webbings, and the like.

These and other objects are realized in accordance with the present invention pursuant to which there is provided a water soluble condensation product of a poly($\alpha$-hydroxyalkyl)phosphorus compound of the formula

or

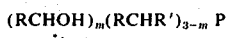

and a nitrogen compound of the formula $RNH_2$, $HO-R''NH_2$ or

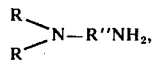

wherein
R is hydrogen or alkyl of 1 to 3 carbon atoms,
R' is OR or

R'' is alkylene of 1 to 3 carbon atoms,
Y is at least one anion selected from the group consisting of chloride, sulfate, phosphate, acetate and formate,
n is an integer from 2 to 4, and
m is an integer from 2 to 3, the phosphorus compound being present in about 0.5 to 6 times the molar amount of the nitrogen compound.

Illustrative poly($\alpha$-hydroxyalkyl)phosphorus compounds are tetrakis(hydroxymethyl)phosphonium chloride, other tetrakis(hydroxymethyl)phosphonium salts, tetrakis($\alpha$-hydroxyethyl)phosphonium acetate, and the like, and especially tris(hydroxymethyl)phosphine.

Illustrations of suitable nitrogen compounds are $NH_3$, methylamine, ethylene diamine, ethanolamine, N,N-dimethylpropylene diamine, and the like. The preferred compounds are methylamine, and especially $NH_3$, because of their low cost and simplicity.

The ratio of the poly($\alpha$-hydroxyalkyl) phosphorus compound to the nitrogen compound must be carefully controlled to maintain water solubility and prevent the formation of insoluble polymers. This ratio varies to some extent with the particular poly($\alpha$-hydroxyalkyl)-phosphorus compound and the particular nitrogen compound used for the preparations. In general the mole ratio of the poly($\alpha$-hydroxyalkyl)phosphorus compound to the nitrogen compound should be in the range of about 6:1 to 0.5:1, preferably about 3:1 to 1:1, to make a water soluble product which is useful for treating textiles for fire retardance.

In general the reaction is performed by dissolving the poly($\alpha$-hydroxyalkyl) phosphorus compound in water and slowly adding to this solution the nitrogen compound with stirring to avoid formation of undesirable, useless insoluble polymer.

If the two compounds reacted were tetrakis(hydroxymethyl)phosphonium chloride and $NH_3$, some of the $NH_3$ would be consumed in neutralizing the acidity of some of the THP salt simultaneously while it reacted with the hydroxymethyl phosphine moiety. When this latter reaction occurs, the chemical linkages will be

in the water soluble condensation product formed. The same type of structure would be formed if one started with tris(hydroxymethyl) phosphine and ammonia or tris(hydroxymethyl)phosphine and methylamine, for example. The preferred phosphorus reactant is tris(hydroxymethyl)phosphine, desirably added as such or optionally formed in situ by first neutralizing a tetrakis-(hydroxymethyl)phosphonium salt preferably with a strong alkali such as sodium hydroxide, followed by reaction with the preferred nitrogen compound, vis. ammonia. When starting with the phosphine, it is often desirable to include formaldehyde in approximately equimolar amount or glyoxal in half that quantity. Unlike use of tetrakis(hydroxymethyl)phosphonium salts, there is no anion present, such anions sometimes resulting in discoloration of the textile material and sometimes necessitating a bleaching step. Alternatively, precursors or liberators of formaldehyde may be used in place of the corresponding amounts of formaldehyde per se, e.g. paraformaldehyde, hexamethylene tetramine, and the like. In using hexamethylene tetramine it also serves as a source of ammonia.

These condensation products are water soluble materials which remain stable for 6 months or longer without any insoluble polymer being formed. They are different from the starting materials as can easily be demonstrated by infrared spectroscopy, thin layer chromatography and other analytical techniques well known to those skilled in the art.

The reaction is preferably effected in aqueous media, thereby directly to form aqueous solutions which can be applied to textiles, optionally after addition of further agents and/or further dilution with water. The amount of water during reaction advantageously is sufficient to form a solution having a water concentration of more than about 20% by weight and advantageously about 25 to 60% by weight.

The water soluble condensation products of this invention include the structure

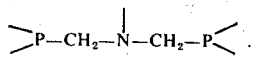

By contrast the Proban structure described hereinabove, made from refluxing tetrakis(hydroxymethyl)-phosphonium chloride and urea, includes the grouping

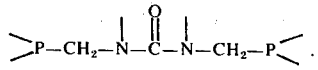

The Ciba-Geigy Pyrovatex 3762 product has the structure

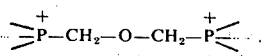

Because the novel products are water soluble and of higher molecular weight than THP salts, they have much less tendency to migrate to the surface of textiles when treated textiles are dried. Their aqueous solutions result in more uniform application of the active material than do applications of aqueous dispersions of water insoluble materials.

The water soluble condensation products of this invention contain methylol groups attached to phosphorus which are capable of reacting further with aminoplast resins, cellulose, etc. to graft them onto cellulose and to form insoluble polymers in and on the textile fabric. This is probably what occurs during the curing of the textile fabric. The fixation of both phosphorus and nitrogen in sufficient amounts is what imparts to the textile flame retardance which withstands multiple launderings.

The water-soluble condensation products of the present invention may be applied by any convenient means to textile materials, alone or in conjunction with about 2 to 50%, preferably about 15 to 40%, in their weight of one or more of (1) aminoplast resins, (2) urea, and (3) thiourea. Normally the application would be made by padding the textile material with aqueous solutions of these products. The textile material is then dried or partially dried and then may be cured by: (1) a chemical cure in which the dried or partially dried fabric is exposed to ammonia — either gaseous or aqueous or a combination of the two; (2) a thermal cure in which the dried or partially dried fabric is subjected to elevated temperature for a time sufficient to fix the condensation products on and in the textile material, usually to a temperature of about 260° to 370°F for about 15 seconds to 10 minutes; or (3) a combination cure in which the dried or partially dried textile materials are exposed first to a thermal cure and then to a chemical cure with ammonia.

The preferred cure is the thermal cure since this requires no special finishing equipment and, surprisingly, in many cases gives a better handle to the fabric. An ammonia cure after a thermal cure, however, increases the durability of flame-retardance to repeated launderings.

The preferred method is to dissolve the condensation product and a methylolmelamine resin in water with a wetting agent and a softener. The textile fabric is padded with this aqueous solution, dried and then thermally cured in an oven. The textile material is thereafter washed in water containing a surfactant and an oxidizing agent such as sodium perborate or a combination of $H_2O_2$ and a base such as sodium silicate to remove unreacted material and improve the flame-retardance of the fabric.

Other than the water soluble condensation products of this invention no product is available to meet the children's sleepwear standard with polyester-cotton blend fabrics which comprise one-third of the total textile fabrics produced in the United States. Textile materials treated in accordance with the invention retain their flame retardance after more than 50 launderings and tumble-dryings when tested according to FF 3-71, the Children's Sleepwear Standard. The novel products are also useful for treating all types of cellulosic materials, wool and blends of cellulosic fibers with wool, mohair, nylon, acrylics, vinyon, modacrylics, and other fiber types.

The amount of condensation product applied to the textile material may be varied widely depending upon the level of flame retardance desired as well as the level of wash fastness desired. Advantageously it will be at least about 5% by weight of the untreated textile material and preferably at least about 10%. It can be as high as about 50% or even higher but little additional benefit is gained by going above about 35%. The pick-up can be adjusted by the concentration of condensation product in the solution employed, which is generally about 20 to about 60% by weight. The composition and construction of the textile as well as the extent of squeezing out of the impregnated textile material can also be used to adjust the pick-up.

The following examples serve to illustrate the practice of the invention, but are not to be considered as limiting:

EXAMPLE 1

125 Parts of an 80% solution of tetrakis(hydroxymethyl)phosphonium chloride in water were added to 50 parts of water and 35 parts of ice. This solution was agitated as 10.7 parts of 28% aqueous ammonia were added gradually over a period of 50 minutes. The temperature rose to 35°C. Formation of a water soluble condensation product was confirmed by thin layer chromatography (TLC). The amounts used correspond to a 3:1 molar ratio of tetrakis(hydroxymethyl)phosphonium chloride to $NH_3$.

EXAMPLE 2

125 Parts of a 80% aqueous solution of tetrakis(hydroxymethyl) phosphonium chloride were added to 50 parts of water and 35 parts of ice. The pH of the solution was adjusted to 6.5 with sodium hydroxide. The solution was then essentially one of tris(hydroxymethyl)phosphine and formaldehyde or an adduct of the two. The solution was stirred as 10.7 parts of 28% aqueous ammonia were added over a period of 5 minutes. Formation of a water soluble condensation product was confirmed by a TLC analysis. The amounts of reacted components corresponded to a 3:1 molar ratio of tris(hydroxymethyl)phosphine:$NH_3$.

EXAMPLE 3

166 Parts of Pyroset TKP, a product which is an aqueous mixture of tetrakis(hydroxymethyl) phosphonium phosphate and tetrakis(hydroxymethyl)phosphonium acetate containing approximately 9.9% phosphonium phosphorus, were added to 35 parts of water and 35 parts of ice. 21.4 parts of 28% aqueous ammonia were added as in Example 1. TLC analysis confirmed formation of a water soluble condensation product. This condensate was formed from reactants having a molar ratio of 1.5:1 phosphonium phosphorus:ammonia.

EXAMPLE 4

A 1:1 molar ratio tetrakis(hydroxymethyl)phosphonium chloride:$NH_3$ water soluble reaction product was formed by addition of 32.1 parts of 28% aqueous ammonia to 125 parts of tetrakis(hydroxymethyl)phosphonium chloride.

EXAMPLE 5

A 1.5:1 molar ratio tetrakis(hydroxymethyl)phosphonium chloride:$NH_3$ water soluble reaction product was formed by adding with agitation 21.4 parts of 28% aqueous ammonia to 125 parts of an 80% aqueous solution of tetrakis(hydroxymethyl)phosphonium chloride and 50 parts water, and heating the resultant solution at 60°C for 1 hour.

EXAMPLE 6

A 0.5:1 molar ratio tetrakis(hydroxymethyl)phosphonium chloride:$NH_3$ water soluble reaction product was formed by adding with agitation 64.2 parts of 28% aqueous ammonia to 125 parts of an 80%. aqueous solution of tetrakis(hydroxymethyl) phosphonium chloride and 50 parts water, and heating the resultant solution to the boil on a hot plate.

EXAMPLE 7

8.2 Parts of monomethylamine were bubbled into 125 parts of an 80% aqueous solution of tetrakis(hydroxymethyl) phosphonium chloride which had previously been adjusted to pH 6.0 with sodium hydroxide. The temperature rose rapidly to 70°C. This corresponds to a 2:1 molar ratio of tetrakis(hydroxymethyl)phosphonium chloride: monomethylamine water soluble condensation product.

EXAMPLE 8

124 Parts of tris(hydroxymethyl)phosphine (93% pure) were dissolved in 250 parts of water. To this were added 86.7 parts of 37% aqueous formaldehyde, after which the pH was adjusted to 7 with concentrated phosphoric acid. Finally 20.3 parts of 28% aqueous ammonia were added to form a 3:1 tris(hydroxymethyl)phosphine:$NH_3$ water soluble reaction product. Water was added to make the solution a total of 571 parts.

EXAMPLE 9

To the reaction product of EXAMPLE 5 there were added enough sodium hydroxide to bring the pH to 5, 30 parts of Resloom HP (a commercial melamine resin which is probably trimethylolmelamine), 0.3 parts of Triton X-100 (a commercial wetting agent which is an alkyl, probably octyl, phenoxy polyethoxyethanol) and water to a total of 300 parts of solution. The solution was padded onto a 5.1-ounce 50-50 polyester-cotton fabric and squeezed to a 90% wet pick-up. The fabric was dried in a forced air oven for 5 minutes at 190°F and subsequently given a heat cure at 280°F for 5 minutes in a forced air oven. The fabric was washed in a home washing machine in 0.1% hydrogen peroxide, 0.01% sodium silicate and 0.01% sodium hydroxide at 60°C for 5 minutes, rinsed and dried. The fabric had a solids add-on of 22.7%. The fabric was laundered and tested according to FF 3-71, the Chilren' s Sleepwear Standard for sizes 0-6X. It showed an initial char length of 1.6 inches and a char length of 3.3 inches after 50 launderings.

EXAMPLE 10

A 3:1 reaction product was formed as in Example 2. The pH of the solution was adjusted to 6.5 with sodium hydroxide. To it were added 22.5 parts of Resloom HP, 0.3 parts of Triton X-100 and water to a total of 300 parts. The solution was padded onto a 5.1 ounce 50/50 polyester/cotton fabric at an 85% wet pick-up. The fabric was dried in a forced-air oven at 190°F for 5 minutes and subsequently heat cured in a forced-air oven for 4 minutes at 290°F. The fabric was then given an ammonia cure by soaking in 10% aqueous ammonia for 5 minutes. The fabric was rinsed, dried, padded with 3% hydrogen peroxide, placed in a sealed plastic bag for 30 minutes, washed in a commercial home washing machine for 5 minutes and finally dried. The add-on of material to the fabric was 19.9%. The fabric was washed and tested according to DOC pFF 5-73, the proposed Sleepwear Standard for children's sleepwear sizes 7–14. The treated fabric was laundered and tested at various intervals with the following: results:

| Number of Launderings | Char Length (inches) |
|---|---|
| 0 | 2.2 |
| 30 | 1.5 |
| 40 | 1.8 |
| 50 | 1.5 |

EXAMPLE 17

A 3:1 tetrakis(hydroxymethyl)phosphonium chloride:$NH_3$ water soluble condensation product was prepared as in Example 2. The pH of the solution was adjusted to 6.0 with sodium hydroxide. To the solution was added 22.5 parts of Resloom HP, 0.3 parts Triton X-100, and water to a total of 300 parts. 50—50 polyester-cotton fabric was padded with this bath, dried 5 minutes at 190°F, cured 5 minutes at 280°F, rinsed in cold water and oxidized as in Example 10. The add-on of material to the fabric was 18.0%. The fabric was laundered and tested as in Example 10 with the following results:

| Number of Launderings | Char Length (inches) |
|---|---|
| 0 | 2.3 |
| 10 | 2.8 |
| 25 | 2.8 |

EXAMPLE 12

A 3:1 tetrakis(hydroxymethyl)phosphonium chloride: $NH_3$ reaction product was formed in a manner similar to that used in Example 2 by using 125 parts of 80% aqueous tetrakis(hydroxymethyl)phosphonium chloride and 21.4 parts of 28% aqueous ammonia. The pH of the solution was adjusted to 6.0 with sodium hydroxide. To the solution were added 19.5 parts Resloom HP, 15 parts of urea, 0.3 parts Triton X-100 and water to a total of 300 parts. The bath was applied to the polyester-cotton blend in the same manner as that described in Example 9 including drying, thermal cure, and oxidation. The fabric has an add-on of 24%. It was laundered and tested as described in Example 10 with the following results:

| Number of Launderings | Char length (inches) |
|---|---|
| 0 | 2.2 |
| 10 | 3.6 |
| 25 | 1.2 |
| 50 | 1.9 |

EXAMPLE 13

A 1.25:1 tetrakis(hydroxymethyl)phosphonium chloride: $NH_3$ reaction product was formed as in Example 2 by using 125 parts of 80% aqueous tetrakis(hydroxymethyl)phosphonium chloride and 25.3 parts of 28% aqueous ammonia. The pH of the bath was adjusted to 5.0 with sodium hydroxide. To the solution were added 42 parts of urea, 0.3 parts Triton X-100, and water to a total of 300 parts. The bath was applied to the polyester-cotton blend fabric in the same manner as in Example 10 including drying, thermal curing, ammonia curing, oxidation and washing. The add-on of material to the fabric was 23%. The fabric was laundered and tested as in Example 5 with the following results:

| Number of launderings | Char Length (inches) |
|---|---|
| 0 | 1.2 |
| 10 | 1.5 |

EXAMPLE 14

A 1.5:1 mole ratio reaction product was formed as in Example 7 by the addition of 21.4 grams of 28% aqueous ammonia to 125 grams of 80% aqueous tetrakis(hydroxymethyl)phosphonium chloride. The pH of the solution was adjusted to 6.0 with sodium hydroxide. To it were added 15 parts of Resloom HP, 0.3 parts Triton X-100 and water to a total of 300 parts. The bath was applied to the 5.1 oz. polyester-cotton blend fabric, padding to a 85% wet pick-up, drying 5 minutes at 190°F, curing 5 minutes at 280°F, and then placing the fabric in a gaseous ammonia atmosphere for 5 minutes. The fabric was subsequently soaked for 5 minutes in 10% aqueous ammonia and oxidized and washed as in Example 10. The add-on of material was 21.0 %. It was laundered and tested as described in Example 10 with the following results:

| Number of Launderings | Char Length (inches) |
|---|---|
| 0 | 2.5 |
| 10 | 2.7 |
| 25 | 2.8 |

EXAMPLE 15

A 3:1 molar ratio of phosphonium compound : ammonia reaction product was made by reacting 166 grams of Pyroset TKP with 10.7 parts 28% aqueous ammonia made in a manner similar to that in Example 3. To this solution were added 22.5 parts of Resloom HP, 0.3 parts of Triton X-100 and water to a total of 300 parts. The bath was applied to the polyester/cotton blend fabric in the same manner as in Example 10 including drying, curing, oxidation and washing. The add-on was 21.0%. It was laundered and tested as described in Example 10 with the following results:

| Number of launderings | Char length (inches) |
|---|---|
| 0 | 1.8 |
| 10 | 1.8 |

EXAMPLE 16

8.2 Parts of monomethylamine were bubbled into 125 parts of 80% aqueous tetrakis(hydroxymethyl)phosphonium chloride which had previously been adjusted to pH 6.0 with sodium hydroxide as in Example 7. To this solution were added 22.5 parts Resloom HP, 0.3 parts Triton X-100 and water to a total of 300 parts. The solution was applied to a polyester/cotton blend fabric in the same manner as in Example 10 including manner of drying, thermal curing, ammonia curing, and oxidizing. The add-on was 20.8%. The fabric was laundered and tested as in Example 10 with the following results:

| Number of launderings | Char length (inches) |
|---|---|
| 0 | 2.4 |
| 10 | 2.1 |
| 30 | 2.3 |

EXAMPLE 17

A 3:1 molar ratio reaction product was formed as in Example 2. The pH of the solution was adjusted to 6.0 with sodium hydroxide. To this solution were added 30 parts of Aerotex Resin 92 (a commercial product which is believed to be an equimolar mixture of mono- and dimethylol melalmine), 0.3 parts Triton X-100 and water to a total of 300 parts. The solution was padded onto a 5.1-ounce 50—50 polyester-cotton fabric to a 90% wet pick-up. The fabric was dried for 5 minutes at 190°F, cured 5 minutes at 280°F and oxidized as in Example 9. The add-on of material to the fabric was 22.6%. The fabric was laundered and tested as in Example 10 with the following results:

| Number of launderings | Char length (inches) |
| --- | --- |
| 0 | 2.5 |
| 25 | 1.2 |

EXAMPLE 18

A 3:1 molar ratio reaction product was formed as in Example 2. To this solution were added 15 parts Resloom HP and 15 parts thiourea, 0.3 parts Triton X-100 and water to a total of 300 parts. This solution was padded onto a 5.1-ounce 50—50 polyester-cotton fabric to a 85% wet pick-up. The fabric was dried 5 minutes at 190°F, cured 5 minutes at 280°F, and chemically cured by soaking in 5% aqueous ammonia for 5 minutes. The fabric was then oxidized as in Example 10. The fabric was laundered and tested as in Example 10 with the following results:

| Number of launderings | Char length (inches) |
| --- | --- |
| 0 | 2.1 |
| 20 | 4.5 |
| 40 | 5.8 |

EXAMPLE 19

A 1:1 molar ratio condensation product was formed from the reaction of 100 grams of 80% tetrakis(hydroxymethyl)phosphonium chloride and 18.9 grams of gaseous dimethylamine. To this product were added 8.6 parts of 28% aqueous ammonia to form a water soluble condensation product. To this were added 21 parts Resloom HP, 0.3 parts Triton X-100 and water to a total of 244 parts. The solution was applied to a 5.1-ounce 50—50 polyester-cotton fabric to an 85% wet pick-up. The fabric was dried, thermally cured, chemically cured and oxidized as in Example 10. The fabric had an add-on of 17.5% and showed a char length of 5.3 inches.

EXAMPLE 20

A 3:1 molar ratio reaction product was formed as in Example 2. The pH was adjusted to 6.5 with sodium hydroxide and to the solution were added 30 parts Resloom HP, 0.3 parts Triton X-100 and water to a total of 300 parts. The solution was padded onto a 3.6-ounce 100% cotton flannelette to 105% wet pick-up. The fabric was dried 5 minutes at 190°F, cured 5 minutes at 310°F and oxidized as in Example 9. The fabric showed an add-on of 27.9%. It was laundered and tested according to FF 3-71 (the Children's Sleepwear Standard for sizes 0-6X) with the following results:

| Number of launderings | Char length (inches) |
| --- | --- |
| 0 | 2.1 |
| 10 | 1.2 |

EXAMPLE 21

To 270 parts of the solution prepared in Example 8 were added 30 parts of Resloom HP. The resulting solution was padded onto a 5.1-ounce 50—50 polyester-cotton fabric to 95% wet pick-up. The fabric was dried 5 minutes at 190°F and cured 5 minutes at 280°F. The fabric was then oxidized as in Example 9. The fabric was laundered and tested as in Example 10 with the following results:

| Number of launderings | Char length (inches) |
| --- | --- |
| 0 | 1.9 |
| 10 | 2.2 |
| 25 | 2.3 |

EXAMPLE 22

A 1.5:1 molar ratio water soluble reaction product was prepared by first adding 25 parts ice and 25 parts of water to 125 parts of an 80% solution of tetrakis(hydroxymethyl)phosphonium chloride, adjusting the pH to 6.0 with sodium hydroxide, and adding 21.4 parts of 28% aqueous ammonia with stirring. To this solution were added 33 parts of Resloom HP, 0.3 parts of Triton X-100, 8.1 parts of Sapamine APN (a commercial softener which is a cationic fatty amide derivative) and water to a total of 300 parts. The bath was padded onto a 5.1-ounce 50—50 polyester-cotton blend fabric to an 85% wet pick-up. The fabric was dried 5 minutes at 230°F, cured 5 minutes at 280°F, and oxidized as in Example 9. The fabric had a handle almost as soft as the untreated fabric. It had an average char length of 2.5 inches after 50 launderings when tested according to FF 3-71, the Children's Sleepwear Standard.

It will be appreciated that the instant specification and examples are set forth by way of illustration and not limitation, and that various modifications and changes may be made without departing from the spirit and scope of the present invention.

What is claimed is:

1. The process for rendering a textile material fire retardant comprising impregnating a textile material with an aqueous solution of a condensation product of a poly($\alpha$-hydroxyalkyl)phosphorus compound of the formula

or

and a nitrogen compound of the formula $RNH_2$, $HD-R'' NH_2$ or

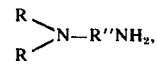

wherein
each R is independently hydrogen or alkyl of 1 to 3 carbon atoms,
R' is OR or

R'' is alkylene of 1 to 3 carbon atoms,
Y is at least one anion selected from the group consisting of chloride, sulfate, phosphate, acetate and formate,
$n$ is an integer from 2 to 4, and
$m$ is an integer from 2 to 3,
the phosphorous compound being present in about 0.5 to 6 times the molar amount of the nitrogen compound, drying the textile material, and curing the textile material by heating.

2. The process of claim 1, wherein R of the phosphorus compound is hydrogen, $n$ is 4, $m$ is 3 and the nitrogen compound is ammonia or methylamine.

3. The process of claim 2, wherein the nitrogen compound is ammonia and the phosphorus compound is present in about 1 to 3 times the molar amount of the ammonia.

4. The process of claim 3, wherein the phosphorus compound is tris(hydroxymethyl)phosphine and approximately 1 mole of formaldehyde or 0.5 mole of glyoxal is present per mole of phosphine.

5. The process of claim 1, wherein the solution contains about 25 to 60% of water by weight.

6. The process of claim 1 wherein there is added to the condensate-containing solution after its formation and prior to impregnation at least one member selected from the group consisting of a melamine formaldehyde resin, urea and thiourea in about 2 to 50% by weight of the condensation product.

7. The process of claim 1, wherein there is added to the condensate-containing solution after its formation and prior to impregnation a melamine formaldehyde resin in about 2 to 50% by weight of the condensation product.

8. The process of claim 1, wherein said textile material comprises a cellulosic fiber, optionally blended with polyester or nylon, the polyester or nylon being present in up to about 75% by weight of the blend.

9. The process of claim 8, wherein said textile material comprises cotton or rayon blended with polyester which is present in about 50 to 65% by weight of the blend, and the phosphorus compound is tris(hydroxymethyl)phosphine.

10. The textile material produced by the process of claim 1.

11. The textile material produced by the process of claim 7.

12. The textile material produced by the process of claim 9.

* * * * *

UNITED STATES PATENT AND TRADEMARK OFFICE
CERTIFICATE OF CORRECTION

PATENT NO. : 3,936,585

DATED : February 3, 1976

INVENTOR(S) : Robert Bruce LeBlacn and Destin A. LeBlanc

It is certified that error appears in the above-identified patent and that said Letters Patent are hereby corrected as shown below:

Col. 8, line 54, cancel "17" and substitute -- 11 --.

Col. 12, line 46, Claim 1, cancel "HD" and substitute -- HO --.

Signed and Sealed this eighteenth Day of May 1976

[SEAL]

Attest:

RUTH C. MASON
Attesting Officer

C. MARSHALL DANN
Commissioner of Patents and Trademarks